(12) United States Patent
Jackson

(10) Patent No.: US 8,928,325 B2
(45) Date of Patent: Jan. 6, 2015

(54) IDENTIFICATION OF ELEMENTAL MERCURY IN THE SUBSURFACE

(75) Inventor: Dennis G. Jackson, Augusta, GA (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 315 days.

(21) Appl. No.: 13/314,348

(22) Filed: Dec. 8, 2011

(65) Prior Publication Data

US 2013/0147489 A1 Jun. 13, 2013

(51) Int. Cl.
*G01V 3/00* (2006.01)

(52) U.S. Cl.
USPC .............................. 324/376; 436/73

(58) Field of Classification Search
CPC ... G01N 33/241; G01N 27/00; G01N 27/002; G01N 27/27; G01N 27/4163; G01N 15/1031; G01N 21/88; G01N 15/0886; E21B 47/026; E02D 1/04
USPC ............................ 324/376, 347, 348; 436/73
See application file for complete search history.

(56) References Cited

U.S. PATENT DOCUMENTS

| | | | |
|---|---|---|---|
| 4,492,111 A * | 1/1985 | Kirkland | 73/84 |
| 5,171,692 A | 12/1992 | Craig, Jr. | |
| 5,497,091 A * | 3/1996 | Bratton et al. | 324/348 |
| 5,757,484 A * | 5/1998 | Miles et al. | 356/318 |
| 5,759,859 A | 6/1998 | Sausa | |
| 5,798,940 A * | 8/1998 | Bratton et al. | 700/267 |
| 5,921,328 A * | 7/1999 | Babineau et al. | 175/20 |
| 6,147,754 A | 11/2000 | Theriault et al. | |
| 6,962,466 B2 | 11/2005 | Vinegar et al. | |
| 8,444,937 B2 * | 5/2013 | Tuli et al. | 422/535 |
| 2003/0138644 A1 * | 7/2003 | Khandros et al. | 428/447 |
| 2009/0324337 A1 | 12/2009 | Ball | |
| 2010/0257920 A1 | 10/2010 | Lee et al. | |

OTHER PUBLICATIONS

M.R. Pinnel, J.E. Bennett, Voluminous oxidation of aluminum by continuous disolution in a wetting mercury film; Journal of Materials Science 7, (1972) pp. 1016-1026.

* cited by examiner

*Primary Examiner* — Huy Q Phan
*Assistant Examiner* — Giovanni Astacio-Oquendo
(74) *Attorney, Agent, or Firm* — J. Bennett Mullinax, LLC

(57) ABSTRACT

An apparatus and process is provided for detecting elemental mercury in soil. A sacrificial electrode of aluminum is inserted below ground to a desired location using direct-push/cone-penetrometer based equipment. The insertion process removes any oxides or previously found mercury from the electrode surface. Any mercury present adjacent the electrode can be detected using a voltmeter which indicates the presence or absence of mercury. Upon repositioning the electrode within the soil, a fresh surface of the aluminum electrode is created allowing additional new measurements.

6 Claims, 2 Drawing Sheets

IDENTIFICATION OF ELEMENTAL MERCURY IN THE SUBSURFACE

STATEMENT AS TO RIGHTS TO INVENTIONS MADE UNDER FEDERALLY SPONSORED RESEARCH AND DEVELOPMENT

This invention was made with Government support under Contract No. DE-AC09-08SR22470 awarded by the United States Department of Energy. The Government has certain rights in the invention.

FIELD OF THE INVENTION

This invention is directed towards a method and apparatus for detecting mercury in subsurface soils.

BACKGROUND OF THE INVENTION

This invention relates to the ability to identify elemental mercury (Hg(0)) in subsurface soils using a soil probe which is driven into the ground. Detection of elemental mercury is important in characterizing possible contamination of current and former industrial sites which utilized mercury.

Current techniques for mercury detection as part of remediation protocols are described in the Vinegar U.S. Pat. No. 6,962,466 entitled "Soil Remediation of Mercury Contamination". This reference discloses using a neutron logging tool as a subsurface probe to determine mercury concentration. The analytical technique uses a spectral analysis to detect mercury.

The Sausa U.S. Pat. Nos. 5,759,859 and the Theriault 6,147,754 US Patent describe cone-penetrometer based systems that are adapted for subsurface spectral analysis using a laser system to generate ions which are identified based upon a spectrum analysis.

Other techniques for detecting mercury soil contamination involve collecting samples of soil which are subsequently analyzed in a laboratory or other field assay techniques which require returning a soil sample to a surface. As taught by Christy U.S. Pat. No. 5,639,956 special percussion driven probes can be used for the collection of such soil samples at multiple depths. However the operation of such equipment is considered to be labor intensive and time consuming.

Accordingly, there remains room for improvement and variation within the art. It is a primary object of the present invention to allow for the detection of elemental mercury at a subsurface level without bringing a soil sample to the surface.

SUMMARY OF THE INVENTION

It is one aspect of at least one of the present embodiments of the invention to provide for a cone-penetrometer based probe that has sensor which establishes an electrical potential when a Hg(0) is contacted in the subsurface.

It is a further aspect of at least one of the present embodiments of the invention to provide for Hg(0) detection device comprising an aluminum electrode, a reference electrode, and a volt meter such that the aluminum electrode will react with Hg(0) to create a measureable potential indicating the presence of Hg(0).

It is a further aspect of at least one of the present embodiments of the invention to provide for a probe, which may be deployed by a cone-penetrometer, the probe having a tip comprising a sacrificial layer of aluminum such that Hg(0) present within the soil will react with the aluminum to produce a measureable electrical potential.

It is yet a further and more particular aspect of at least one embodiment of the present invention to provide for a direct-push/cone-penetrometer based probe having a sacrificial aluminum tip electrode which can react with mercury present within the soil. A feature of the sacrificial aluminum electrode is that as the direct-push system advances the sensor to a new subsurface depth, the abrasive action of the insertion removes mercury from the aluminum interface and thereby eliminates the voltage potential. In this manner, the cone-penetrometer and the aluminum tip electrode of the probe can be used to detect the presence or absence of elemental mercury at a new depth within the subsurface.

It is a further aspect of at least one of the present embodiments of the current invention to provide for a process of detecting elemental mercury which comprises the steps of: supplying a probe having a terminal end defining an aluminum electrode; inserting the probe to a desired depth within a subsurface region; allowing elemental mercury that may be present in a subsurface soil to react with aluminum electrode, thereby creating an electric potential; measuring the electrical potential as an indication of elemental mercury being present; and thereafter, inserting the probe to a new location within a subsurface, the insertion process removing mercury from the surface of the aluminum electrode allowing the electrode to detect the presence of mercury at the new below ground location.

It is a further aspect of at least one of the present embodiments of the present invention to provide for a cone-penetrometer based probe having a sacrificial aluminum electrode tip in which the process of inserting the electrode tip into a subsurface region removes naturally occurring oxides present from the surface of the aluminum thereby providing an aluminum electrode surface that is reactive with elemental mercury that may be present in the subsurface.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

DESCRIPTION OF THE PREFERRED EMBODIMENT

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents.

Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus, or process pathway. To avoid redundancy, detailed descriptions of much of the apparatus once described in relation to a figure is not repeated in the descriptions of subsequent figures, although such apparatus or process is labeled with the same reference numbers.

Figure 1:
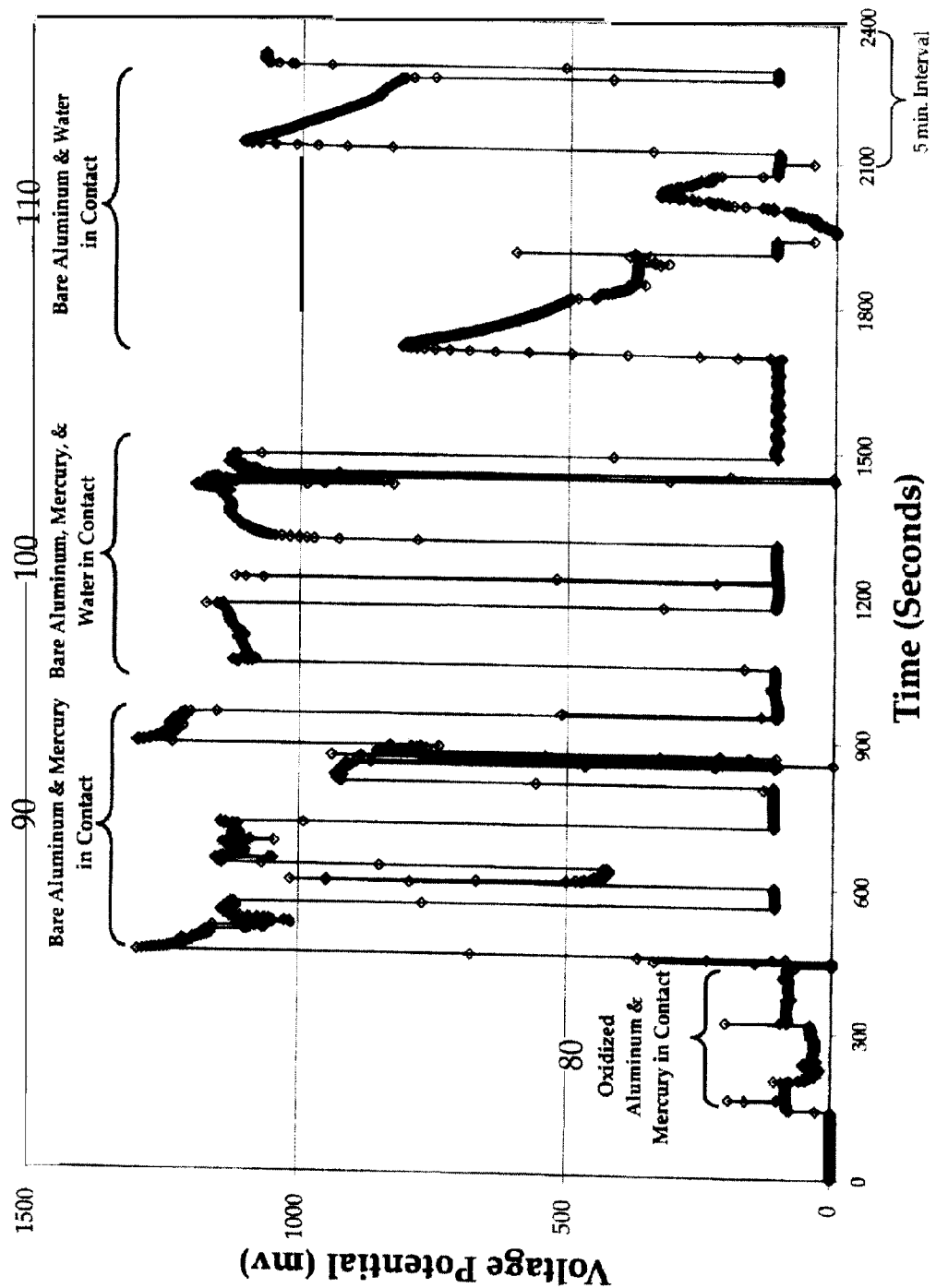
FIG. 1 is a graph setting forth voltage response curves for oxidized aluminum and elemental mercury, bare aluminum and elemental mercury.

As seen in reference to FIG. 1, an elemental mercury probe 10 is provided and seen in the form of a direct-push/cone-penetrometer based sensor. The probe has an aluminum tip 20 which may assume any number of typical configurations of a cone-penetrometer based probe. Tip 20 is formed of aluminum which would react with oxygen under ambient conditions to form a coating of aluminum oxide 22. When the probe is inserted into a subsurface region, the insertion through the soil abrades the aluminum tip and removes the oxide coating. Upon removal of the oxide coating, the newly exposed aluminum electrode tip surface can react with elemental mercury present within a subsurface region. As used herein, the term "aluminum" as applied to the probe can include pure aluminum or aluminum alloys. Any suitable aluminum alloy which is reactive with elemental mercury and capable of forming a measureable voltage potential can be utilized with the present invention. It would be a matter of routine experimentation for one having ordinary skill in the art to evaluate various aluminum alloys in order to determine appropriate alloys for use as a sensor.

As further seen in reference to FIG. 1, an insulating ring 30 is used to isolate the aluminum tip 20 from a main body portion 40 of the steel cone-penetrometer rod 60. A first electrical lead 50 was used to provide electrical activity between the aluminum electrode tip 20 and a voltmeter 70 which may be positioned in an above ground rotation. A second electrical lead 52 connects the voltmeter to reference electrode which may be in the form of a steel rod which may be used in the construction of and/or the deployment of the cone-penetrometer sensor.

Figure 2:
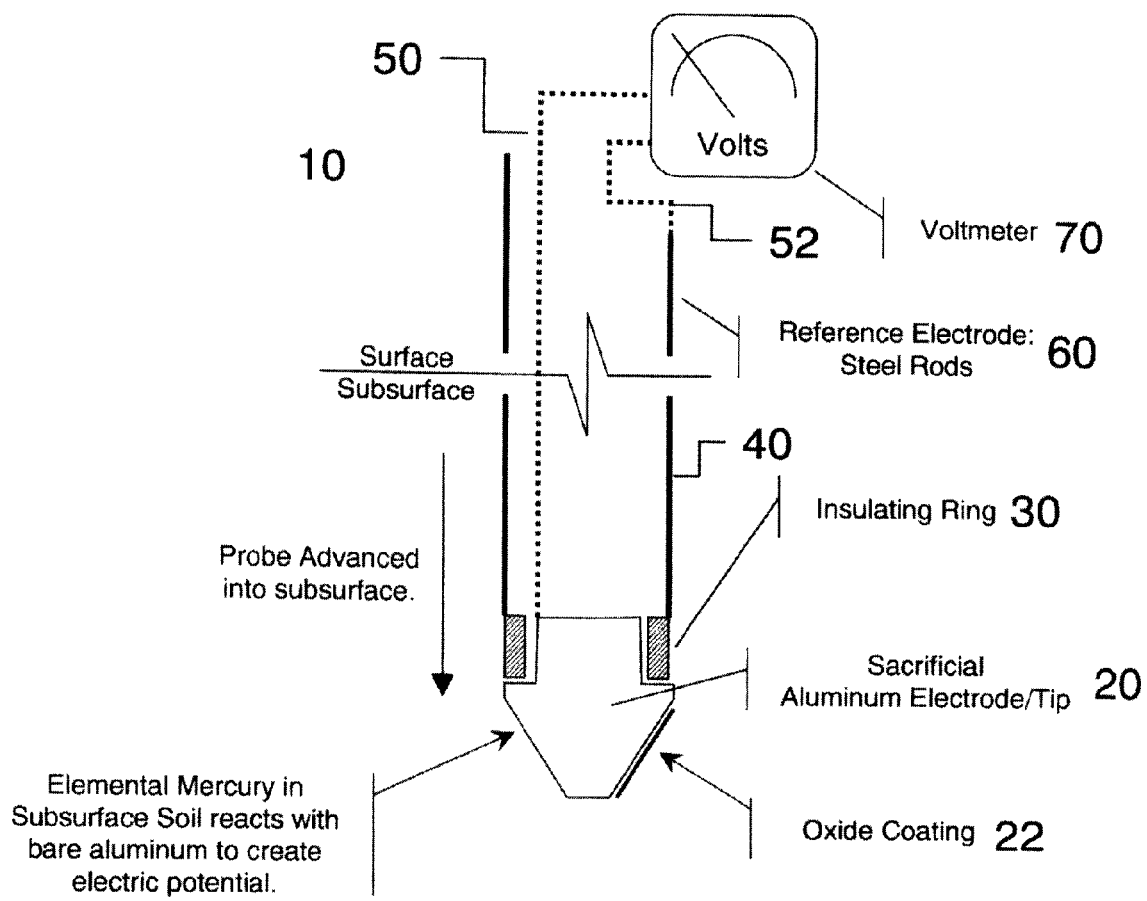
FIG. 2 is a schematic drawing setting forth one embodiment of a mercury detector in form of a cone-penetrometer probe.

When the probe 10 is deployed below ground, the abrasion of the sacrificial aluminum electrode removes any surface oxide and allows the aluminum surface to interact with elemental mercury. As seen in reference to FIG. 2 the interaction of the oxidized aluminum with mercury creates a voltage potential below 100 mv 80. With the surface oxidation removed, the bare aluminum interacts with mercury to create a voltage potential in excess of 1,000 mv 90. When a small amount of water is present the resulting potential is clear and consistent response signal of 100. When no mercury is present the bare aluminum and water creates a potential that decays below 1,000 mv 110. The decay is actually the result of aluminum oxide layer reforming on the surface and creating a new insulating layer.

The voltage potential created through the interaction of elemental mercury and bare-aluminum serves as a sensor that provides a qualitative assay that detects the presence of elemental mercury via its interaction with the bare aluminum surface. The ability of elemental mercury to react with an aluminum surface so as to create an electromotive potential is described in U.S. Pat. No. 5,171,692 which is incorporated herein by reference. Reaction of the mercury with the aluminum electrode is not a depletion reaction in that it provides an ongoing unique and constant voltage signal when elemental mercury is detected.

One advantage of the present sensor configuration is the ability to sacrificially remove an outer layer of aluminum electrode tip thereby cleaning the tip of either oxides which would render the tip unresponsive to mercury or by removing previously reacted elemental mercury from the surface of the aluminum electrode tip. The abrasion and resistance of the probe being inserted into the subsurface has been found adequate to remove sufficient layers such that the electrode tip once again becomes responsive to the presence of elemental mercury at a second lower ground location. Mercury is unique in that it acts like a catalyst in this reaction and prevents aluminum oxides from "attaching" to bare aluminum, preventing the formation of a subsequent oxide layer.

The deployment of the probe using a cone-penetrometer need only extend a few inches in order to remove a sufficient amount of the sacrificial material from the electrode to carry out the mercury detection protocols. As used herein, the term "sacrificial amount" is defined as the amount of the surface of the aluminum electrode that must be removed, including any surface oxide or bound elemental mercury, such that the surface of the aluminum electrode will be responsive to elemental mercury present within the soil. When elemental mercury is present within a subsurface soil, the reaction time is instantaneous. The aluminum surface will react with elemental mercury under a wide variety of subsurface conditions.

While the exemplary embodiment is directed to a process and apparatus using a cone-penetrometer based probe having a single aluminum electrode tip as a sensor, it is envisioned that additional aluminum electrodes could be formed at spaced locations along the edge wall of the device. It is believed that having one or more aluminum electrodes defined along the arcuate exterior wall of the device will function in a similar manner to the tip electrode. The abrasive movement through the soil substrate will similarly remove the oxides from the surface of aluminum electrodes defined in the sidewall of the device. By spacing electrodes a known distance along the edge wall, one can obtain multiple readings at known depth following a single deployment of the device. Once the readings are taken, the device can be inserted deeper within the soil substrate using cone-penetrometer type equipment thereby obtaining new values based upon the plurality of electrodes.

The exemplary embodiments above are directed to a process and apparatus using a cone-penetrometer system for the deployment and advancement of the probe. There are a multitude of such systems for deployment of such probes into subsurface environs including but not limited to the various types of cone-penetrometers. In-addition, there exists percussion hammer equipment and direct-push systems of suitable configuration to support deployment of the probe into the soil substrate, all of which are well known by those of ordinary skill in the art.

The present invention is useful for determining both a vertical profile of elemental mercury contamination and can also be used to map the horizontal zone of contamination. For instance, removing the claimed device from a first bore and establishing a second bore at a distance from the first bore will allow the mapping of mercury along a horizontal reference point as well as characterizing elemental mercury present within a vertical dimension. The ability to rapidly and accurately assess the presence of elemental mercury in a below ground location is beneficial for both site characterization of possible elemental mercury contamination as well as carrying out post remediation assays to determine the effectiveness of the remedial efforts. For instance, there are a variety of techniques known in the art to either remove elemental mercury from soil or to chemically alter elemental mercury to a less harmful form. The present invention allows rapid quantification of the efficacy of such remediation techniques.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

That which is claimed:

1. An apparatus for detecting the presence of elemental mercury in a below ground substrate comprising:
    a probe adapted for deployment within a soil substrate, the probe_having a sacrificial aluminum electrode, the sacrificial aluminum electrode having an exposed surface adapted for the sacrificial removal of oxide layers or previously reacted elemental mercury layers from the aluminum electrode surface to establish a chemically reactive surface for elemental mercury to be detected;
    a reference electrode in operative engagement with the aluminum electrode;
    a voltmeter responsive to the aluminum electrode and the reference electrode such that in the presence of elemental mercury the elemental mercury will interact with the aluminum electrode and create a measureable potential on the voltmeter; and
    wherein, the apparatus can detect elemental mercury at multiple locations within a below ground substrate without removal of the apparatus to clean the electrode.

2. A process of detecting elemental mercury in soil comprising the steps:
    supplying a cone-penetrometer system including a probe having a terminal end defining an aluminum electrode;
    inserting the probe to a desired depth within a subsurface region thereby removing oxides from a surface of the aluminum electrode;
    allowing elemental mercury that may present in a subsurface soil to react with the aluminum electrode, thereby creating an electrical potential;
    measuring the electric potential as an indication of elemental mercury being present;
    and thereafter, placing the probe to a new location within a subsurface, with the placing step using an abrasive soil substrate to remove a sacrificial layer of oxides from the surface of the aluminum electrode in order to bring about a chemically reactive surface for elemental mercury to be detected; and,
    allowing the aluminum electrode to detect the presence of additional mercury at the new below ground location.

3. The process according to claim 2 wherein said step of inserting the probe within a subsurface region further removes any previously elemental mercury from the surface of the aluminum electrode.

4. The process according to claim 2 wherein said step of supplying a probe further defines supplying a probe having at least two sacrificial aluminum electrodes defined along a length of the probe.

5. An apparatus for detecting the presence of elemental mercury in a below ground substrate comprising:
    a probe adapted for insertion into a soil substrate, the probe having a sacrificial aluminum electrode and positioned on at least one of a tip of a probe or an edge wall of the probe, the sacrificial aluminum electrode having an exposed surface adapted for the sacrificial removal of oxide layers or previously reated elemental mercury layers from the aluminum electrode surface to establish a chemically reactive surface for elemental mercury to be detected;
    a reference electrode in operative engagement with the sacrificial aluminum electrode;
    a voltometer responsive to the aluminum electrode and the reference electrode such that elemental mercury present within a soil will interact with the aluminum electrode to create a measureable potential on the voltometer; and
    wherein, the apparatus can detect elemental mercury at multiple locations within a below ground substrate without removal of the apparatus to clean the electrode.

6. The apparatus according to claim 5 wherein the apparatus defines a plurality of aluminum electrodes positioned along a length of the probe.

* * * * *